United States Patent
Lombardo et al.

(10) Patent No.: US 6,228,091 B1
(45) Date of Patent: *May 8, 2001

(54) METHODS AND TOOLS FOR TIBIAL INTERMEDULLARY REVISION SURGERY AND ASSOCIATED TIBIAL COMPONENTS

(75) Inventors: Alan Lombardo, Elmwood Park; Stuart L. Axelson, Jr., Succasunna, both of NJ (US); James V. Bono, Dover, MA (US); Kenneth A. Krackow, Williamsville, NY (US)

(73) Assignee: Stryker Technologies Corporation, Kalamazoo, MI (US)

(*) Notice: Subject to any disclaimer, the term of this patent is extended or adjusted under 35 U.S.C. 154(b) by 0 days.

This patent is subject to a terminal disclaimer.

(21) Appl. No.: 09/454,553

(22) Filed: Dec. 7, 1999

Related U.S. Application Data

(62) Division of application No. 09/170,572, filed on Oct. 13, 1998, now Pat. No. 6,063,091.

(51) Int. Cl.⁷ .................................................. A61B 17/56
(52) U.S. Cl. .................................. 606/88; 606/86; 606/87
(58) Field of Search ................................ 606/79, 80, 86, 606/87, 88, 96

(56) References Cited

U.S. PATENT DOCUMENTS

| | | | |
|---|---|---|---|
| 4,678,471 | | 7/1987 | Noble et al. ............... 623/16 |
| 5,047,061 | | 9/1991 | Brown ...................... 623/23 |
| 5,275,603 | * | 1/1994 | Ferrante et al. ........... 606/86 |
| 5,290,313 | * | 3/1994 | Heldreth ................... 623/20 |
| 5,290,315 | | 3/1994 | DeCarlo, Jr. ............... 623/22 |
| 5,342,367 | * | 8/1994 | Ferrante et al. ........... 606/86 |
| 5,356,414 | * | 10/1994 | Cohen et al. ............... 606/88 |
| 5,417,695 | | 5/1995 | Axelson, Jr. .............. 606/89 |
| 5,464,406 | * | 11/1995 | Ritter et al. ................ 606/86 |
| 5,578,039 | * | 11/1996 | Vendrely et al. ........... 606/88 |
| 5,609,642 | * | 3/1997 | Johnson et al. ............ 623/20 |
| 5,613,970 | * | 3/1997 | Houston et al. ............ 606/88 |
| 5,634,927 | * | 6/1997 | Houston et al. ............ 606/96 |
| 5,681,316 | * | 10/1997 | DeOrio et al. ............. 606/88 |
| 5,690,636 | * | 11/1997 | Wildgoose et al. ......... 606/88 |
| 5,782,920 | | 7/1998 | Colleran ................... 623/18 |
| 5,788,701 | * | 8/1998 | McCue ..................... 606/88 |
| 5,908,424 | * | 6/1999 | Bertin et al. .............. 606/88 |

FOREIGN PATENT DOCUMENTS

| | | |
|---|---|---|
| 0 820 739 | 1/1998 | (EP) . |
| 0 853 930 | 7/1998 | (EP) . |

\* cited by examiner

*Primary Examiner*—Paul J. Hirsch
*Assistant Examiner*—Michael B. Priddy
(74) *Attorney, Agent, or Firm*—Lerner, David, Littenberg, Krumholtz & Mentlik, LLP

(57) ABSTRACT

IM tibia revision tools include a trial stem extender having multiple notches which serve both as depth witness marks and holders for a stop clip, a collection of different sized tibial templates, each template adapted to receive an angular offset positioning guide, a collection of offset bushings, each bushing each bushing having a different offset distance and each being adapted to cooperate with the trial stem extender and the angular offset positioning guide, a neutral bushing for locating the position of the implant boss relative to the tibia and for reaming the tibia to accept the boss of the implant, a fin punch guide and fin punch for preparing the tibia to receive the keel of the tibial component, and a tool for translating the angular offset measurement to the tibial component. Tibial components according to the invention have three parts: the baseplate portion, the offset portion, and the stem portion. Each portion is provided in a variety of sizes and the portions may be mixed and matched according to the measurements made with the tools described above. Methods for using the tools and the tibial components are also disclosed.

27 Claims, 11 Drawing Sheets

METHODS AND TOOLS FOR TIBIAL INTERMEDULLARY REVISION SURGERY AND ASSOCIATED TIBIAL COMPONENTS

This application is a divisional of U.S. Ser. No. 09/170,572 filed Oct. 13, 1998 now U.S. Pat. No. 6,063,091.

This application is related to co-owned co-pending Ser. No. 09/049,708, filed Mar. 28, 1998, entitled Methods and Tools for Femoral Imtermedullary Revision Surgery, the complete disclosure of which is hereby incorporated herein by reference.

BACKGROUND OF THE INVENTION

1. Field of the Invention

The invention relates to methods and tools used in knee arthroplasty. More particularly, the invention relates to methods and tools used in revision surgery where an artificial tibial component is removed and replaced. The invention also relates to improved tibial components.

2. Brief Description of the Prior Art

Total knee arthroplasty involves the replacement of portions of the patellar, femur and tibia with artificial components. In particular, a proximal portion of the tibia and a distal portion of the femur are cut away (resected) and replaced with artificial components. As used herein, when referring to bones or other body parts, the term "proximal" means closest to the heart and the term "distal" means more distant from the heart. When referring to tools and instruments, the term "proximal" means closest to the practitioner and the term "distal" means more distant from the practitioner.

There are several types of knee prostheses known in the art. One type is sometimes referred to as a "resurfacing type". In these prostheses, the articular surface of the distal femur and proximal tibia are "resurfaced" with respective metal and plastic condylar-type articular bearing components. These knee prostheses provide adequate rotational and translational freedom and require minimal bone resection to accommodate the components within the boundaries of the available joint space.

The femoral component is a metallic alloy construction (cobalt-chrome alloy or 6A14V titanium alloy) and provides medial and lateral condylar bearing surfaces of multi-radius design of similar shape and geometry as the natural distal femur or femoral-side of the knee joint.

The tibial component usually includes a distal metal base component and a proximal interlocking plastic, e.g. UHM-WPE (ultra high molecular weight polyethylene), component or insert. The plastic tibial plateau bearing surfaces are of concave multi-radius geometry to more or less match the articular geometry of the mating femoral condyles. Both the femoral and tibial components are usually provided with intermedullary (IM) stem options.

After preparing the distal surface of the femur and the proximal surface of the tibia, an opening is made into the medullary canal of the femur, and an opening is made into the medullary canal of tibia. The interior surface and the IM stem of the femoral component are usually covered with a polymeric cement and the IM stem is inserted into the medullary canal of the femur until the interior surface of the femoral component meets the distal surface of the femur. The tibial component is similarly usually cemented to the proximal surface and medullary canal of the tibia.

Occasionally, the components are press fit without the use of cement. The use of cement has advantages and disadvantages. Press fit components rely on bone quality to obtain good fixation. Sometimes it is impossible to obtain good fixation with a press fit component and sometimes a press fit component will fail early because of failure of successful biological ingrowth. Cement assures good fixation but puts strain along the component stem. In addition, as described below, cement complicates the removal of a failed component.

Often, due to normal wear over time, the prosthetic knee must be replaced via a procedure known as revision surgery. When the primary cemented prosthetic is removed, the proximal surface of the tibia and the distal surface of the femur typically exhibit cavernous defects. Absent the use of bone graft, the proximal surface of the tibia and the distal surface of the femur must be carefully resected to remove cavernous defects before a replacement knee can be installed.

In addition, the intramedullary (IM) canals must be broached or reamed to remove any remaining cement or cavernous defects existing in the canals before a replacement knee can be installed.

According to the state of the art, after the primary prosthetic is removed, the proximal tibia is resected with a lateral template. The medullary canal is reamed and the reamer is tapped in place with a mallet. A proximal resection guide is attached to the reamer and proximal resection is completed via slots in the guide. Preparation of the distal femur is described in the above referenced related application.

The defects in the tibia are measured and the cutting guide is moved down 6 to 10 mm. A flat cut from anterior to posterior is made. A tibial template is attached to the reamer and reference marks are typically in pen. A flat cut and sagittal cut are made relative to the reference marks. Another template is attached to the reamer and anterior and posterior holes are drilled for securing a wedge resection guide. A wedge cut is then made. The template is replaced and aligned with the marks. A revision mask punch guide is attached to the template and a revision box chisel is used to prepare for a stem.

Those skilled in the art will appreciate that revision surgery is difficult because (1) the type and location of cavernous defects make it difficult to match the exterior surfaces of the tibia and femur to the interior surfaces of the prosthetic, (2) the femur and tibia must be resected with reference to the IM canal, and (3) the use of multiple templates and guides during the course of the procedure makes it very difficult to keep all the cuts in proper alignment relative to the IM canal.

In particular, with respect to the tibia, resection of the proximal tibia results in the creation of a tibial plateau in which the IM canal is no longer centrally located. If a normal tibial component is installed, portions of the tibial component will overhang the resected tibial plateau.

In order to compensate for this problem, it is known in the art to provide tibial components with offset IM stems. However, the relative location of the IM canal relative to the perimeter of the tibial plateau may be offset in any direction, anterior, posterior, medial, or lateral, depending on the individual bone. It is impossible or at least impractical to provide an offset stem tibial component for every possible variation in the relative location of the IM canal.

Moreover, it is difficult to estimate the offset of the IM canal in order to choose an appropriate offset tibial component.

According to the state of the art, offset tibial components are selected by trial and error, a tedious procedure which prolongs surgery. For example, as shown in FIG. 1, a relatively symmetrical tibial plateau 10 exhibits the IM canal 12 in a central location. After resection of the tibial plateau, the location of the IM canal may be located off center as shown in FIGS. 2 and 3 where canals 12' and 12" are seen to be located off center relative to the plateaus 10' and 10" respectively.

SUMMARY OF THE INVENTION

It is therefore an object of the invention to provide methods and tools for performing IM revision surgery.

It is also an object of the invention to provide tools for IM revision surgery which maintain proper alignment with the IM canal while multiple resection cuts are made, tools for determining the offset location of the IM canal relative to the tibial plateau, tools which enhance the accuracy of IM revision surgery and enhance the stability of the revision implant.

It is another object of the invention to provide methods for performing IM revision surgery in which a minimum number of tools are used.

The methods and tools of the invention provide accurate location of bone cuts so that the revision prosthetic is correctly oriented relative the IM canal and the bone cuts. Moreover, the tools and methods provide accurate measurements for use in selecting the appropriate tibial component and for adjusting the angular offset of the tibial component according to the measurements. Additional objects and advantages of the invention will become apparent to those skilled in the art upon reference to the detailed description taken in conjunction with the provided figures.

DETAILED DESCRIPTION

An illustrative embodiment of the invention is set forth hereinafter. The illustrative embodiment makes reference to specific measurements for tool diameters, cut depths, etc., which are intended only to give those skilled in the art an appreciation for the operating principals of the invention without any intent of limiting the spirt or scope thereof. It is applicants' intention that the invention only be limited by the appended claims and not any of the exemplary measurements set forth in the illustrative embodiment of the invention.

According to the methods of the invention, the previous tibial component is removed from the tibia and the IM canal of the tibia is reamed as described in the parent application hereto.

Figure 1:
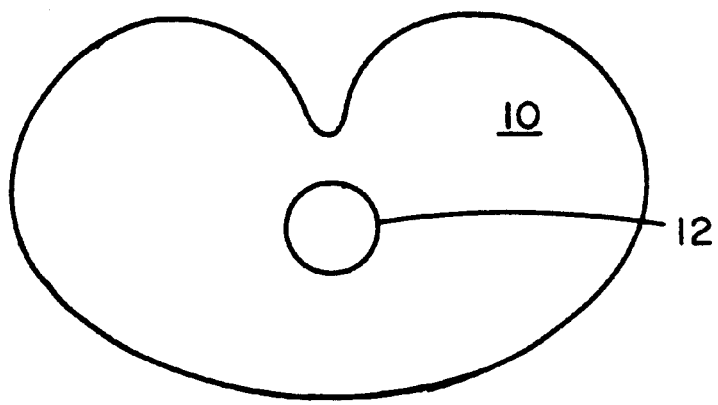
FIG. 1 is a schematic plan view of a relatively symmetrical tibial plateau.
Figure 2:
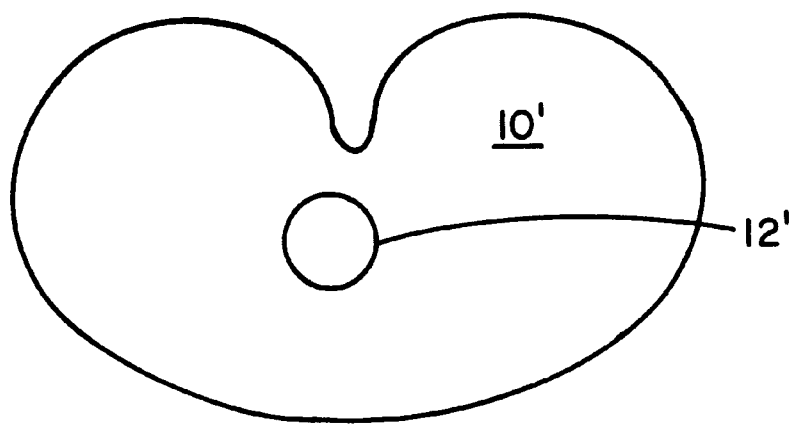
FIG. 2 is a view similar to FIG. 1 showing a slightly offset IM canal.
Figure 3:
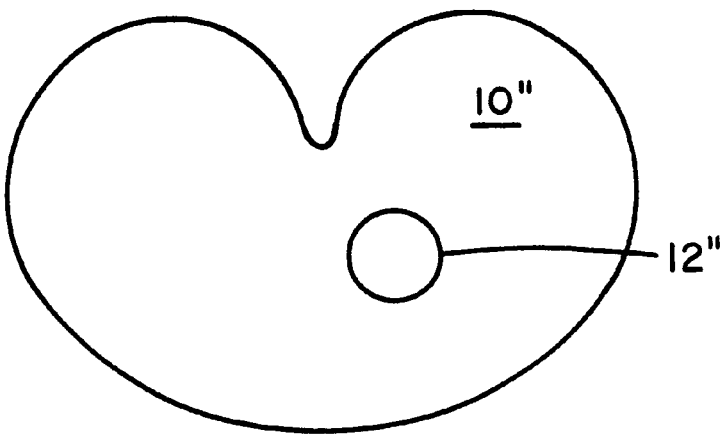
FIG. 3 is a view similar to FIG. 1 showing a more dramatically offset IM canal.
Figure 4:
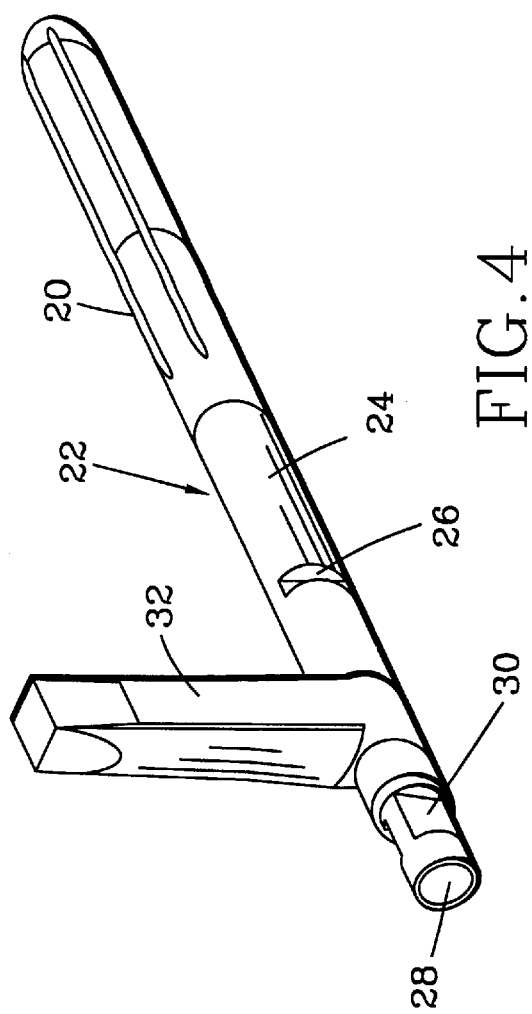
FIG. 4 is a perspective view of the resection guide tower attached to the tool stem.

Referring now to FIG. 4, after the tibial IM canal is prepared, based on the diameter and reaming depth of the last IM reamer used, an appropriate tool stem 20 is chosen for attachment to the resection guide tower 22. The tower 22 has a boss 24 with a pair of surface grooves 26, a stem 28 with a pair of surface grooves 30, and an upstanding shaft 32 therebetween. The boss 24 has interior threads (not shown) and the stem 20 is provided with engaging exterior threads (not shown). According to one embodiment of the invention, the boss 24 has a diameter of 15 mm and several stems 20 of different diameter are provided for attachment to the tower 22.

Figure 5:
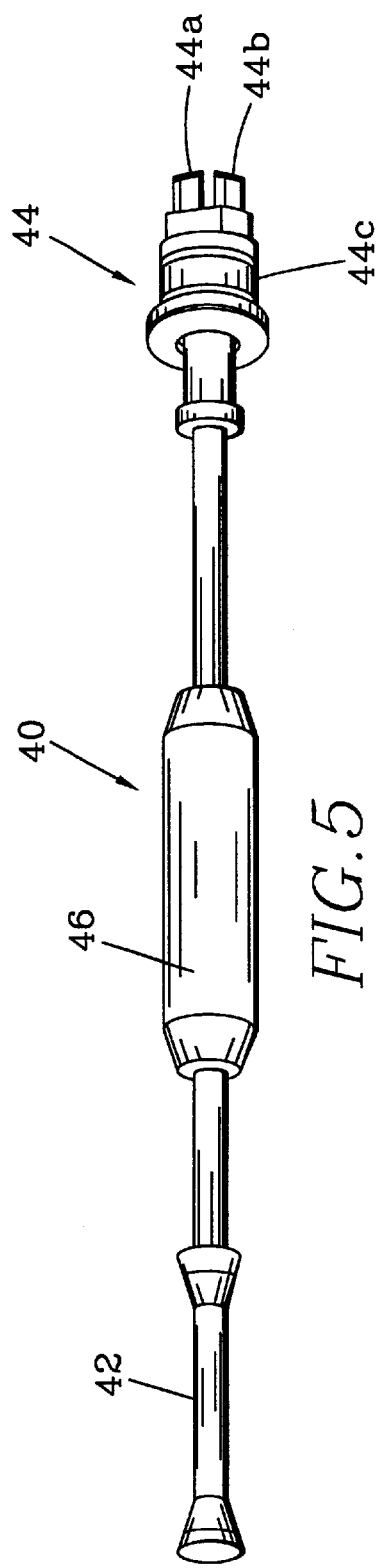
FIG. 5 is a perspective view of the impactor/extractor.
Figure 6:
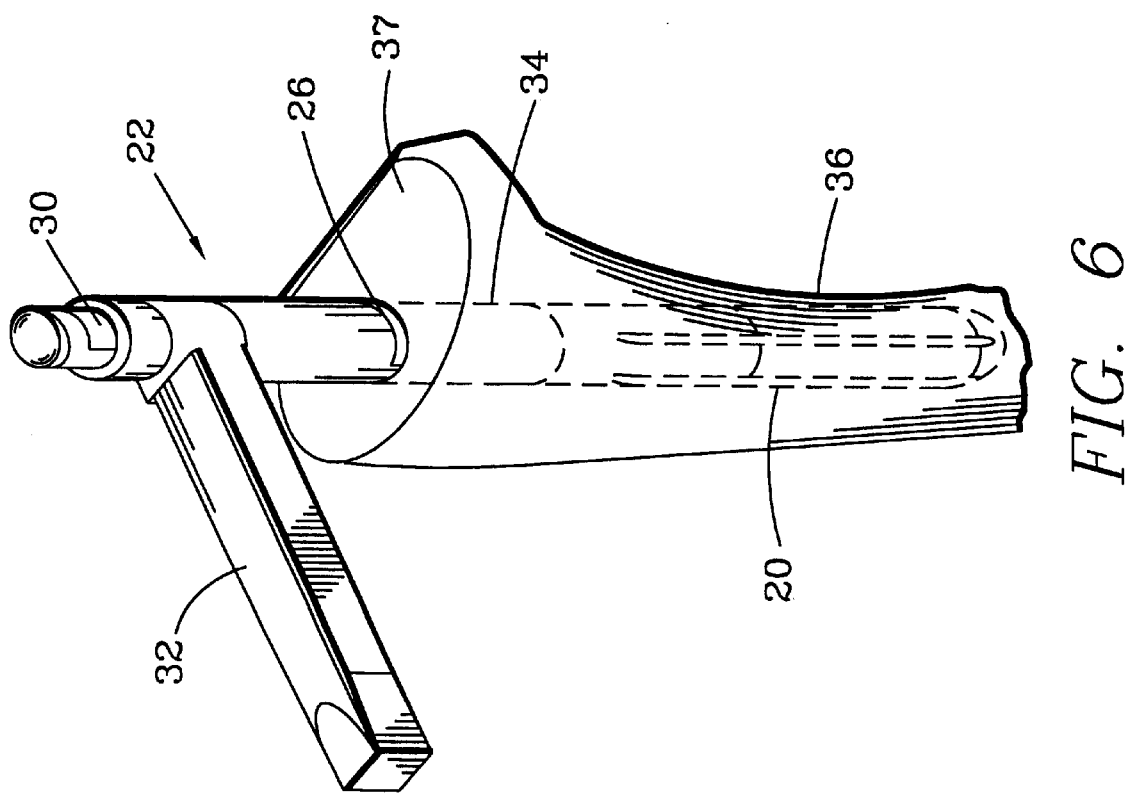
FIG. 6 is a broken perspective transparent view of the guide tower installed in the IM canal of the tibia.

Turning now to FIGS. 5 and 6, the resection guide tower 22 with the attached tool stem 20 is installed in the IM canal 34 of the tibia 36 with the aid of the impactor/extractor 40. The tool 40 has a proximal handle 42, a distal coupling 44, and a sliding mass 46. The coupling 44 has a slot 44a which is dimensioned to receive the stem 28 of the tower 22, and a pair of distal shoulders 44b which are dimensioned to fit into the slots 30 of the stem 28. A spring loaded latch 44c is located adjacent to the slot 44a.

The tool 40 is removably attached to the tower 22. The stem 20 of the tower is then inserted into the IM canal 34 and the sliding mass 46 of the tool 40 is slid distally. The force of the accelerated mass 46 impacts the coupling 44 and drives the stem 20 of the tower 22 into the IM canal 34. If necessary, the mass is slid several times until the stem 22 is fully inserted into the IM canal 34. After the tower is installed, as shown in FIG. 6 the impactor/extractor tool is uncoupled from the tower.

Figure 7:
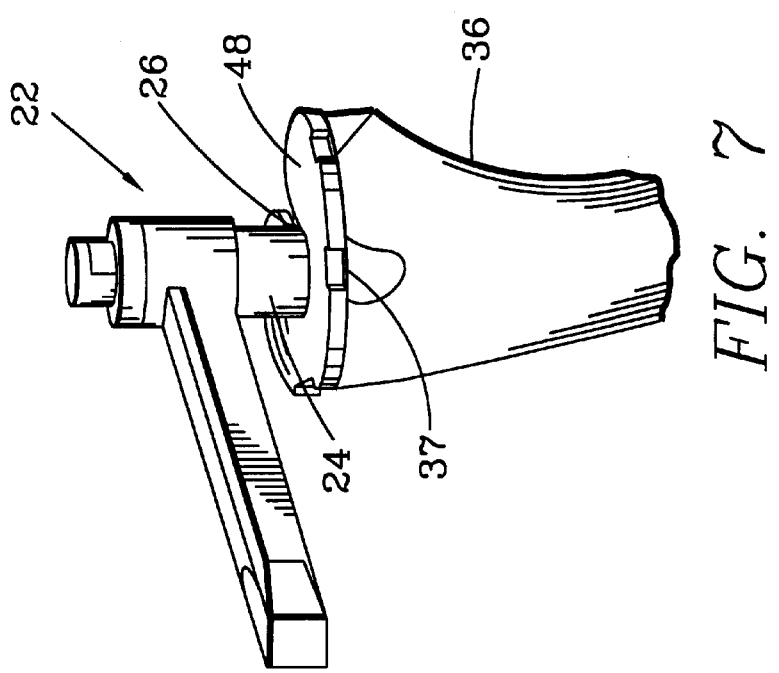
FIG. 7 is a view similar to FIG. 6 with the optional collar attached to the tool stem.

In situations where the IM canal opening is enlarged and does not provide adequate support or a good reference point to seat the tower, a tibial collar 48, shown in FIG. 7, is attached to the boss 24 by engaging the grooves 26. The tibial collar 48 is shaped and dimensioned to cover the tibial plateau 37. In addition to stabilizing the tower 22, the collar 48 aids in preliminary sizing of the tibial plateau 37.

Figure 8:
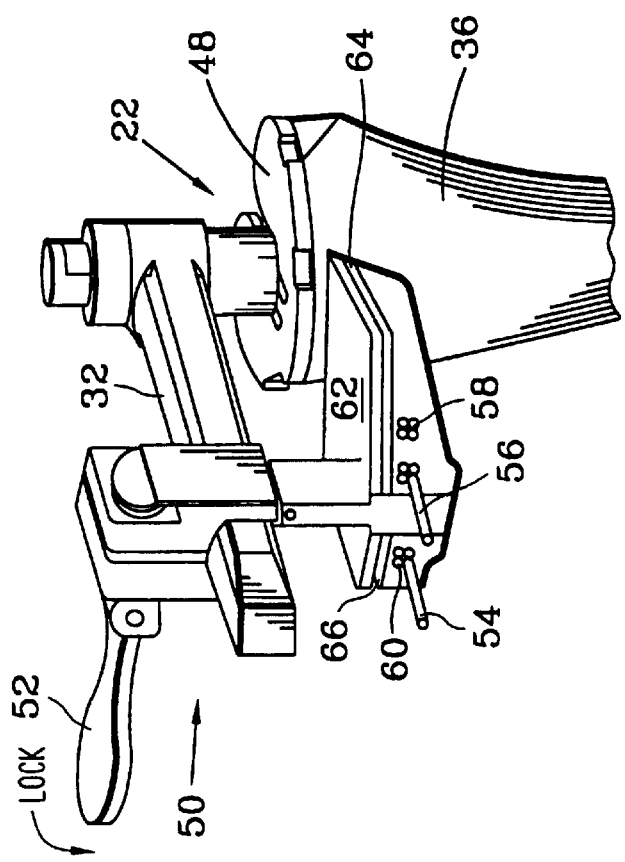
FIG. 8 is a broken perspective view of the cutting block attached to the tool stem.
Figure 9:
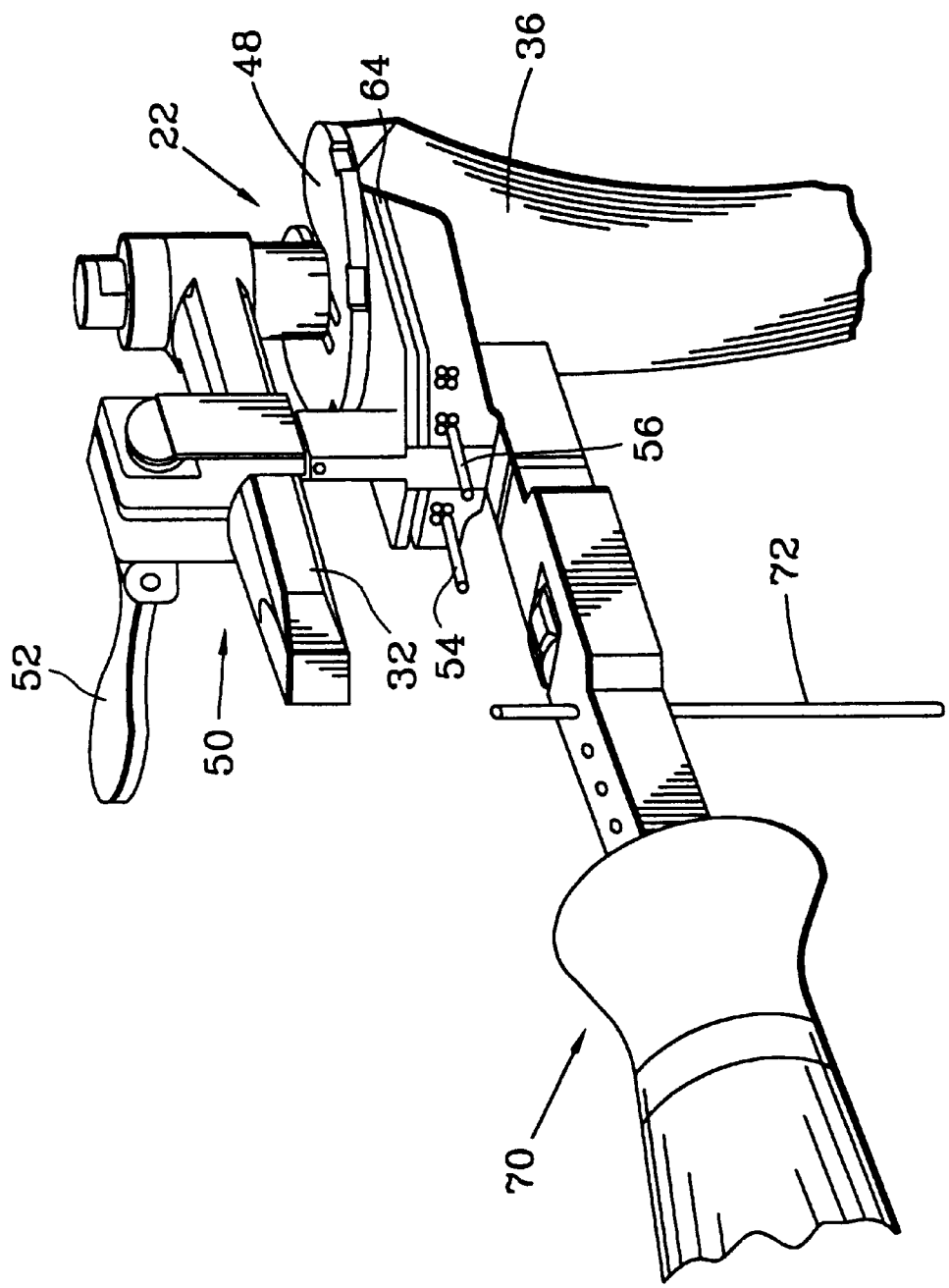
FIG. 9 is a view similar to FIG. 8 showing the optional extra medullary referencing tool attached to the cutting block.

Once the tower 22 is properly installed, a tibial cutting block 50 (which is provided in separate left and right versions) is attached to the upstanding shaft 32 of tower 22 as shown in FIGS. 8 and 9 by means of a cam lock 52 and the two ⅛" drill bits 54, 56 inserted into holes 58, 60. If desired, as shown in FIG. 9, a handle 70 and rod 72 are attached to the cutting block 50 so that an optional visual EM alignment inspection can be made.

With the cutting block 50 so secured, a typical 2 mm clean-up cut can be made using the proximal surface 62 of the cutting block as a guide. According to a preferred embodiment of the invention, three degrees of posterior slope is built into the cutting block and this is why separate left and right cutting blocks are provided. Slots 64, 66 are provided for optional wedge cuts. After the clean-up cut and wedge cuts (if desired) are made, the cutting block 50 and the tower 22 are removed from the tibia 36. The removal of the cutting block and tower is effected with the aid of the impactor extractor 40.

Figure 10:
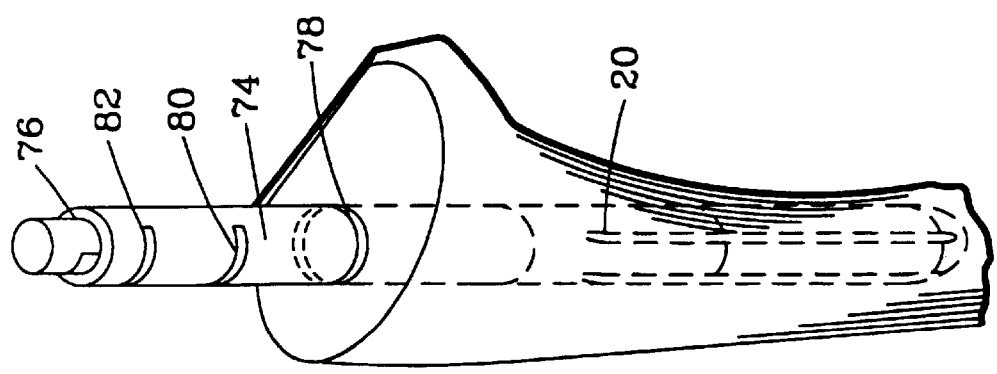
FIG. 10 is a broken perspective transparent view of a trial stem extender and trial stem inserted into the IM canal of the tibia.

Turning now to FIG. 10, after the cutting block and tower are removed from the tibia, a trial stem extender 74 is attached to the trial stem 20 (or another trial stem of the same size). The trial stem extender has a proximal coupling 76 for coupling to the impactor/extractor, and three pairs of circumferential grooves 78, 80, 82 which serve as witness marks and receivers for a stop clip (described below with reference to FIG. 14). The witness marks are useful in determining the length of the stem portion of the tibial component implant.

Figure 11:
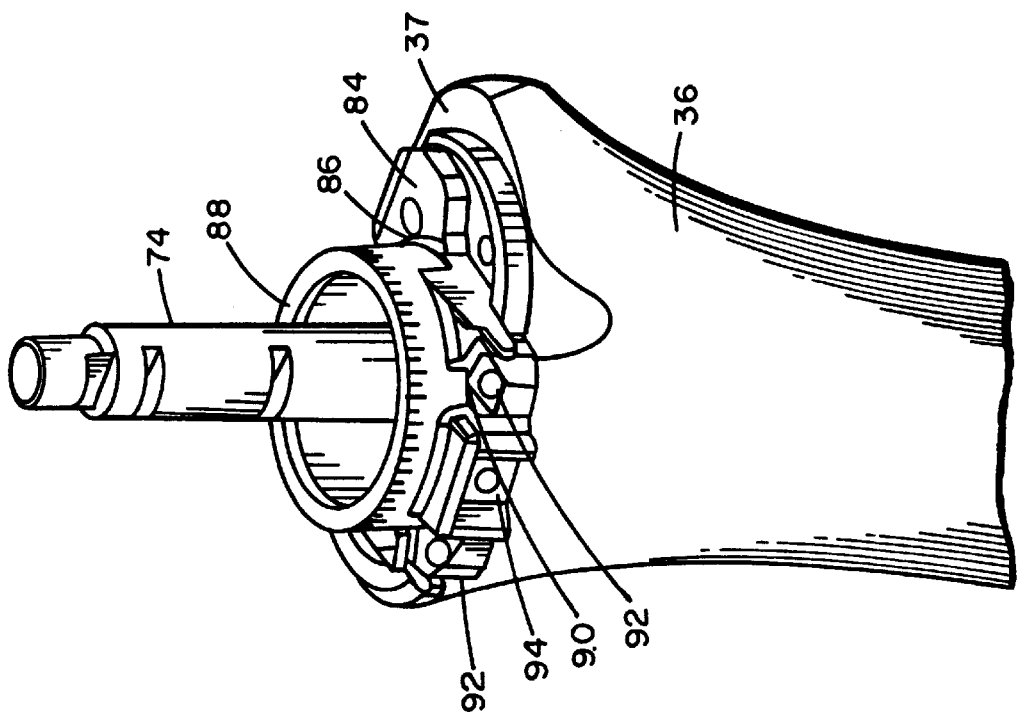
FIG. 11 is a broken perspective view showing the tibial template and offset positioning guide placed over the trial stem on the tibial plateau.

With reference to FIG. 11, with the trial stem and extender 74 in place, an appropriately sized tibial template 84 is selected. The templates 84 are provided in a variety of sizes to correspond to different sized tibial plateaus 37. The size of the template 84 chosen may be based on the size of the collar 48 chosen above. According to the invention, therefore, several different sized templates 84 are provided. Each template 84 has a central circular opening 86 of standard size for receiving the offset positioning guide 88. The offset positioning guide 88 is a generally cylindrical member with a plurality of circumferential markings 90 which indicate angles between 0 degrees and 360 degrees. For clarity, the angle values are not shown in the drawing, except for FIG. 15 which only shows one angle value.

In the presently preferred embodiment, the angle markings 90 are spaced 5 degrees apart (i.e. there are seventy-two markings about the perimeter of the offset positioning guide 88). As suggested by FIG. 15, in the preferred embodiment, the angle values are provided for every other angle marking 90. The tibial template 84 is also provided with a plurality of pin receiving holes 92 (described below with reference to FIG. 15), and a coupling 94 for an optional EM alignment guide (like the guide 70, 72 shown in FIG. 9).

Figure 12:
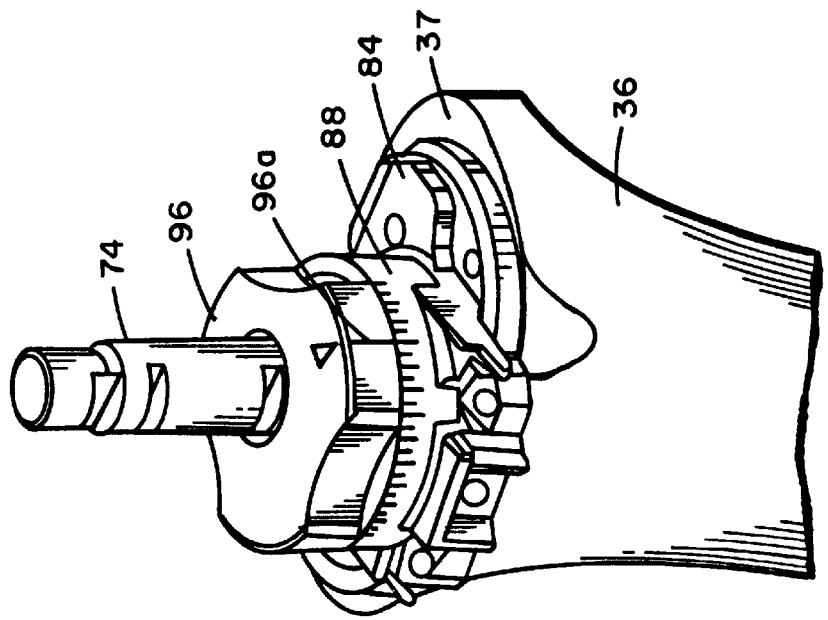
FIG. 12 is a view similar to FIG. 11 showing the 4 mm offset bushing installed in the angular offset positioning guide.
Figure 13:
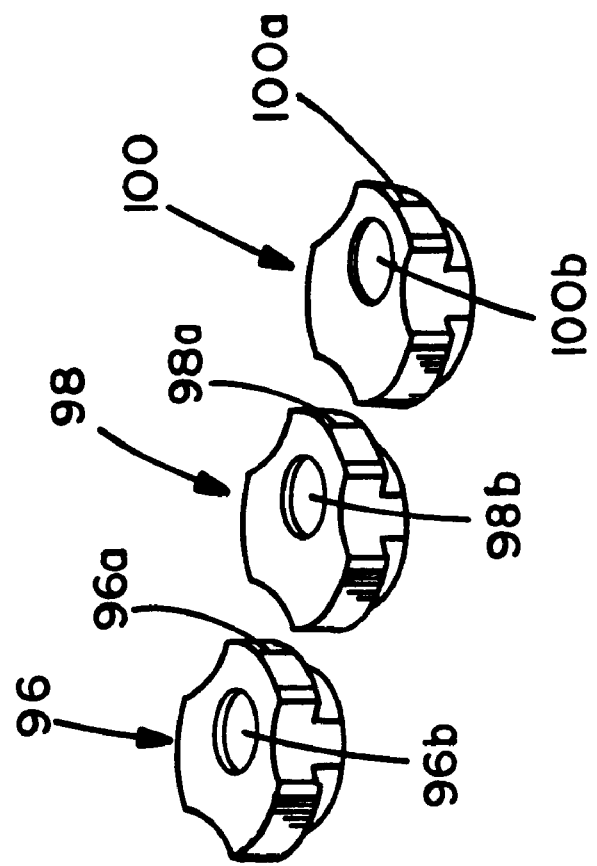
FIG. 13 is a perspective view of the 4 mm, 6 mm. and 8 mm offset bushings.

Turning now to FIGS. 12 and 13, the tools of the illustrative embodiment of invention include three offset bushings 96, 98, 100. Each bushing is a substantially cylindrical member which is dimensioned to fit within the cylindrical offset positioning guide 88 as shown in FIG. 12.

Each bushing 96, 98, 100 is provided with a circumferential indicator 96a, 98a, 100a and a throughbore 96b, 98b, 100b which is designed to receive the trial stem extender 74. According to the invention, the throughbores are not centrally located relative to the center of the cylindrical bushings. Each bushing 96, 98, 100 has a throughbore 96b, 98b, 100b which is offset a different amount from the center of the cylindrical bushing.

According to the presently preferred embodiment, bushing 96 has a 4 mm offset, bushing 98 has a 6 mm offset, and bushing 100 has an 8 mm offset. The circumferential indicators 96a, 98a, 100a are preferably located on the same radius along which the throughbores 96b, 98b, 100b are offset.

Figure 14:
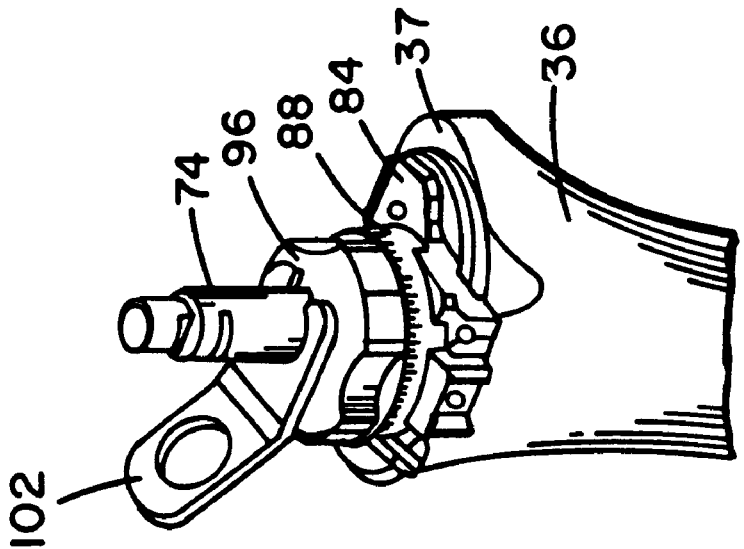
FIG. 14 is view similar to FIG. 12 showing the optional stop clip attached to the trial stem extender.

As shown in FIGS. 12 and 14, an appropriate offset bushing, e.g. 96, is chosen and fitted into the cylindrical offset positioning guide 88 with the trial stem extender 74 extending through the throughbore, e.g. 96b. The appropriate bushing is chosen by visual assessment or by trial and error. Optionally, if the trial stem and extender 74 are unstable in the IM canal, a stop clip 102 may be attached to one of the grooves in the extender 74 as shown in FIG. 14.

With the extender 74, template 84, cylindrical offset positioning guide 88, and bushing 96 assembled as shown, the bushing is rotated relative to the cylindrical offset positioning guide 88 until the template 84 assumes a position relative to the tibial plateau 37 where there is minimum or no overhang. When the optimal (best) position is obtained, the template 84 is pinned to the tibia 36, for example with ⅛" drill pins (or headed nails) 104 through he pin receiving holes 92. The angle indicated by the indicia 96a and 90 is noted before the bushing 96 and stem with extender 74 are removed.

According to the invention, a neutral (boss reaming) bushing 106 is provided. The neutral bushing 106 is substantially the same size and shape as the offset bushings 96, 98, 100, but has a centrally located throughbore 107 and no radial indicia. The purpose of the neutral bushing is to act as a guide for reaming a hole in the center of the tibial plateau 37 for receipt of the boss portion of the tibial implant. Those skilled in the art will appreciate from the foregoing that the location of the center of the "boss hole" will be offset from the tibial IM in the angular direction indicated by the indicators 90, 96a at the step shown in FIG. 15 by an amount equal to the offset amount of the bushing 96 (e.g. 4 mm).

Figure 17:
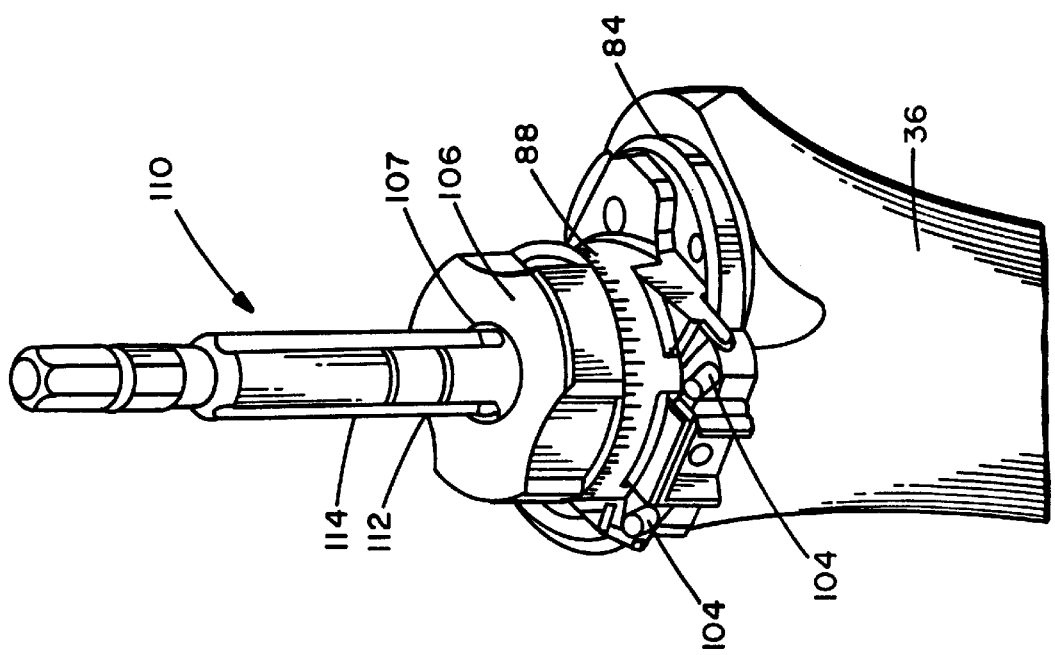
FIG. 17 is a view similar to FIG. 16 showing the boss reamer (or optionally an offset boss reamer) in the reamer bushing.

Turning now to FIG. 17, with the template 84 pinned to the tibia 36 by drill pins 104 and with the neutral bushing 106 inserted in the offset positioning guide 88, a boss reamer 110 (or optionaly an offset boss reamer) is inserted into the throughbore 107 of the neutral bushing 106. The illustrative boss reamer 110 shown in FIG. 17 is 15 mm in diameter and has two depth markings shown, 112 and 114. All of the tibial baseplates according to the illustrative embodiment of the invention have a 15 mm diameter boss, but different baseplates have bosses with different lengths.

Having chosen the appropriately sized template 84, the practitioner will know which tibial baseplate will be used in the implant and will know how deep to ream the hole for the boss of the baseplate. Thus, at this stage of the method of the invention, the practitioner uses the reamer 110 to ream to the appropriate depth indicated by the appropriate depth mark 112 or 114.

Figure 18:
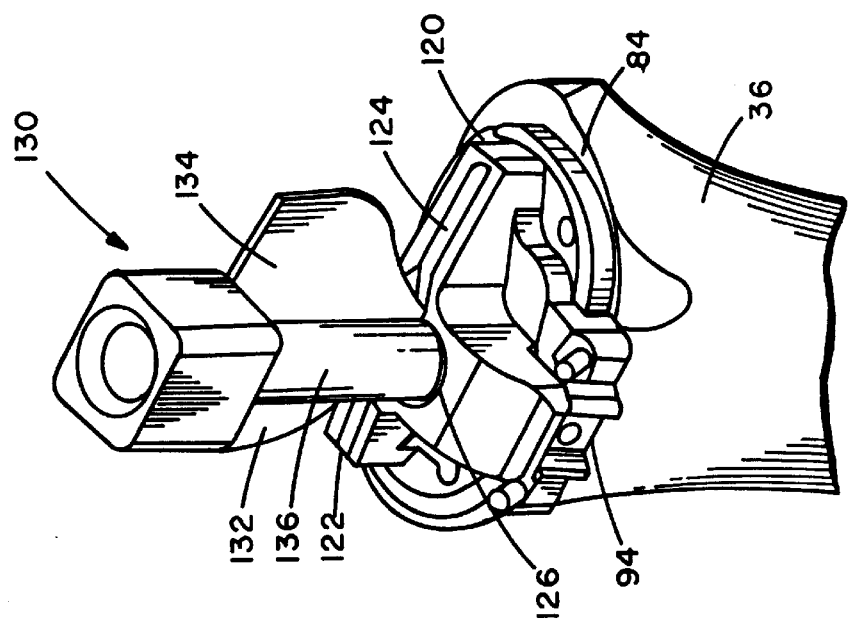
FIG. 18 is a view similar to FIG. 17 with the reamer, bushing, and angular offset guide removed from the template and with the fin punch guide and fin punch in their place.

After reaming for the baseplate boss, the tibia is punched to make space for the baseplate fins or "keel". The boss reamer 110, the neutral bushing 106, and the offset positioning guide 88 are removed and the template 84 is left pinned to the tibia. The fin punch guide 120, shown in FIG. 18, is attached to the template 84. The guide 120 has left and right fin guides 122, 124 and a central boss guide 126. The fin punch 130 has left and right fins 132, 134 and a central boss 136.

The punch 130 is inserted into the punch guide 120 as shown in FIG. 18 with the central boss 136 entering the central boss guide 126 and the left and right fins 132, 134 entering the left and right fin guides 122, 124. With the punch 130 in place, it is struck with a mallet (or attached to the impactor/extractor), driven into the tibial plateau, and then removed. Optionally, if a wedge cut had not been performed at the start (i.e. during the steps described with reference to FIGS. 8 and 9), a wedge cutting guide (not shown) may be attached to the coupling 94 of the template 84 and a wedge cut performed at this stage of the procedure.

Figure 19:
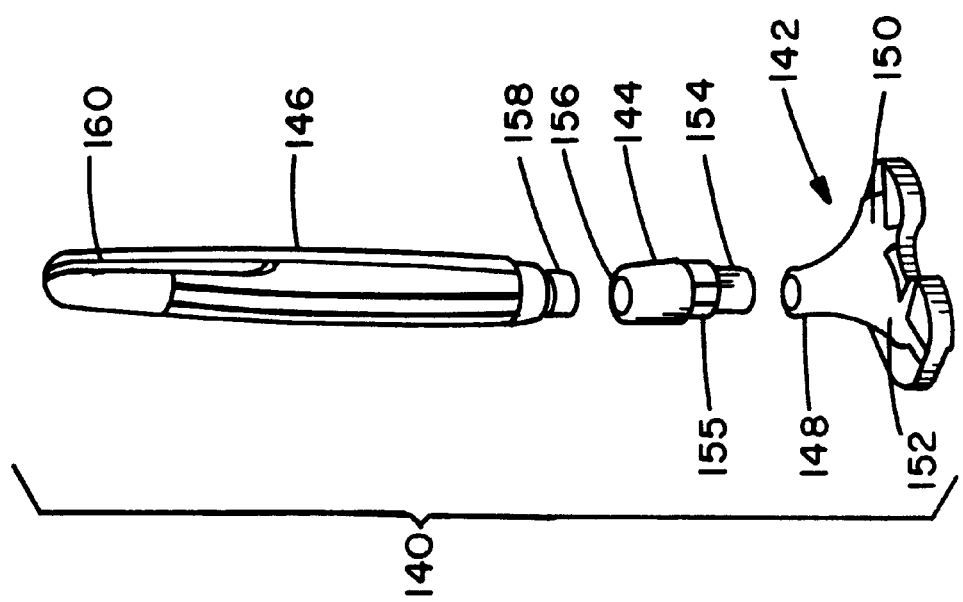
FIG. 19 is an exploded perspective view of a tibial component according to the invention.

All of the apparatus are now removed from the tibia and the tibial component is prepared for implant into the tibia. As mentioned above and as shown in FIG. 19, the tibial component 140 includes the baseplate portion 142, the offset portion 144, and the stem portion 146. It will be appreciated that the tibial component 140 is shown inverted and exploded in FIG. 19 to illustrate the manner in which it is assembled rather than the manner in which it is implanted.

The baseplate 142 can be seen to have a central boss 148 and a pair of fins 150, 152. The offset portion 144 has a male coupling 154 which engages the boss 148, and a female coupling 156 which mates with the stem portion 146. The axes of the couplings 154 and 156 are offset by a certain amount, e.g. 4 mm, 6 mm, or 8 mm, corresponding to the offset bushings 96, 98, 100 shown in FIG. 13 and described above. Between the male coupling 154 and the female coupling 156 is a tightening nut 155 which is used to lock the angular position of the two couplings relative to each other as described in detail below with reference to FIGS. 21 and 22.

Figure 20:
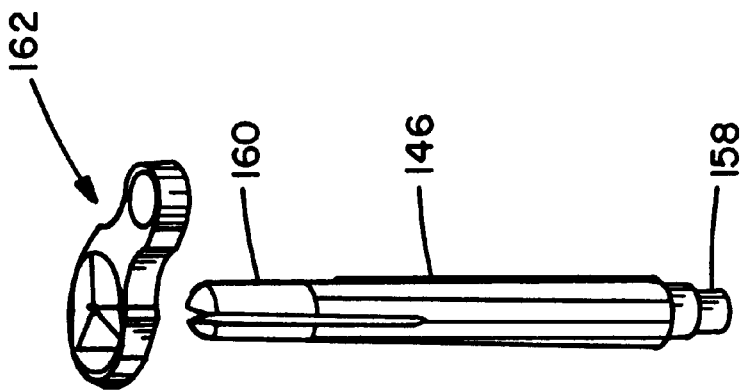
FIG. 20 is an exploded perspective view of the component stem and wrench.

According to the presently preferred embodiment, the stem 146 has a male coupling 158 at its proximal end and a trifurcated distal end 160. The fluted stem 146 is preferably coupled to the offset component 144 with the air of a trifluted wrench 162 which is shown in FIG. 20.

Figure 21:
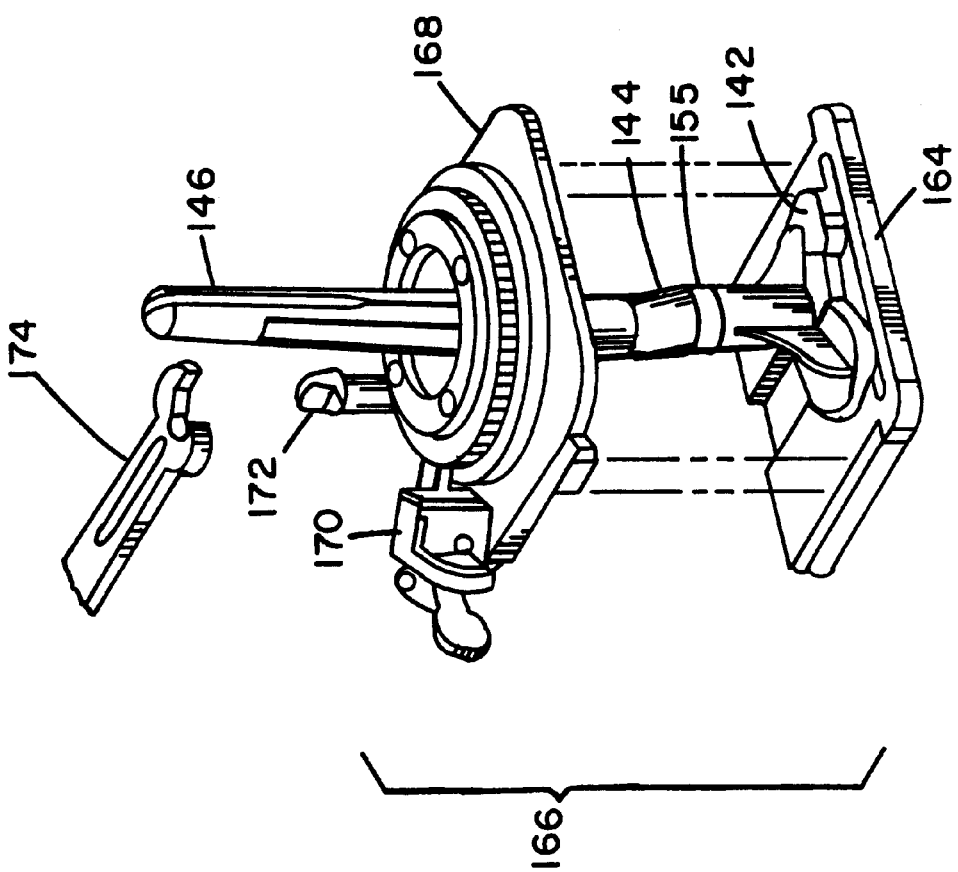
FIG. 21 is an exploded perspective view of the tibial component and the tool for translating the angular offset to it.

Turning now to FIG. 21, the offset portion 144 is fixedly attached to the stem portion 146 and loosely coupled to the baseplate portion 142. The baseplate portion 142 is placed in the base 164 of an angular adjustment tool 166. A turntable portion 168 of the tool 166 is placed over the stem portion 146, the offset portion 144 and tightening nut 155, engaging both the base 164 and baseplate portion 142. The turntable 168 has a locking knob 170 and an angle indicator/wrench key 172.

Figure 15:
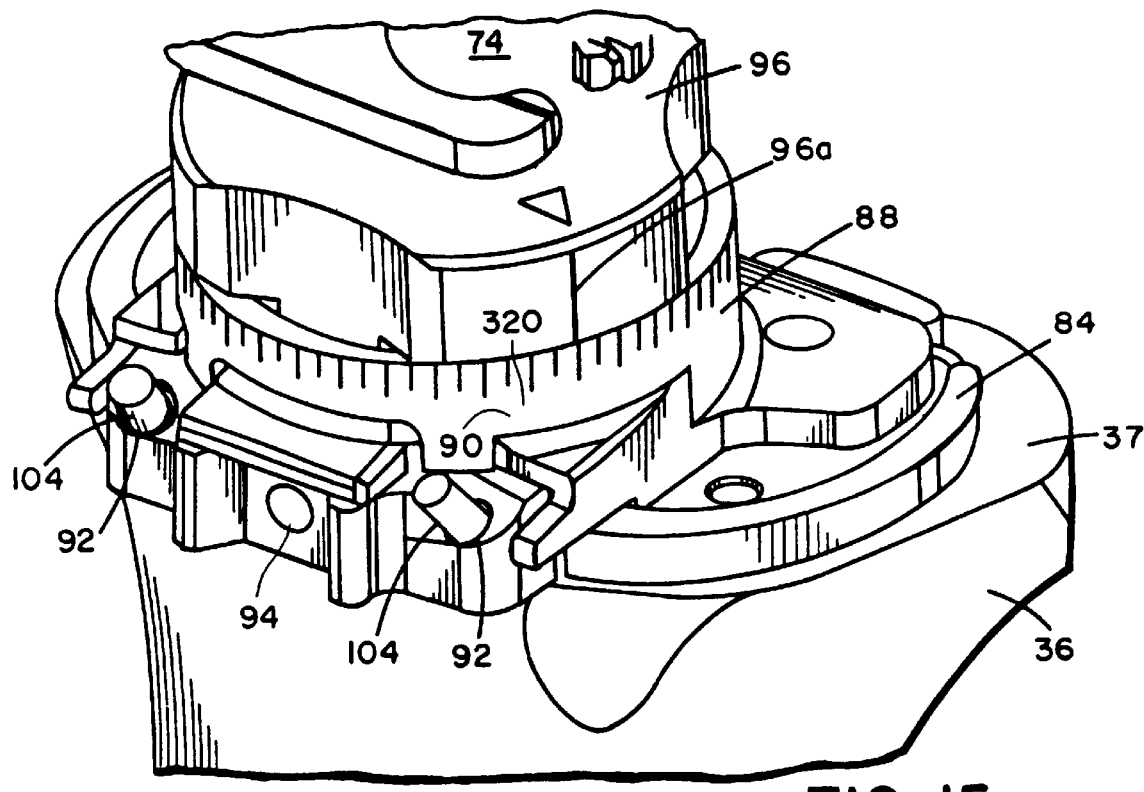
FIG. 15 is an enlarged broken perspective view of the 4 mm offset bushing installed in the angular offset positioning guide indicating an angular offset of 320 degrees and showing the template pinned to the tibia.
Figure 16:
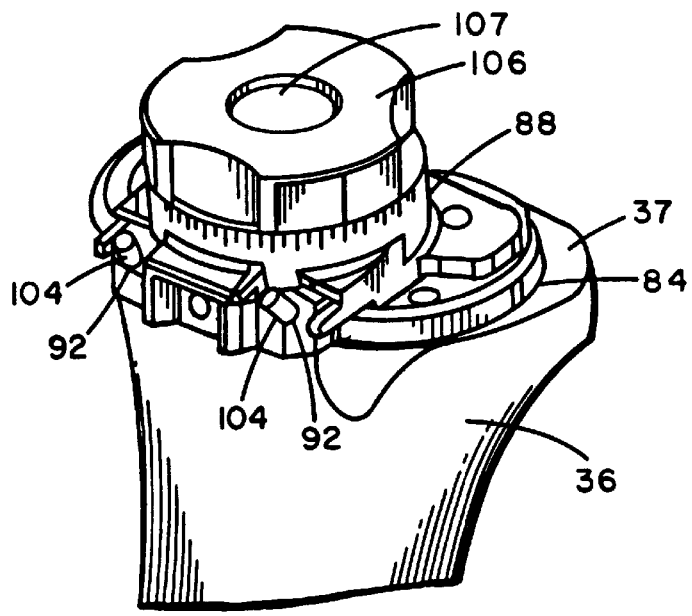
FIG. 16 is a view similar to FIG. 15 showing the 4 mm offset bushing removed and the boss reamer bushing in its place.
Figure 22:
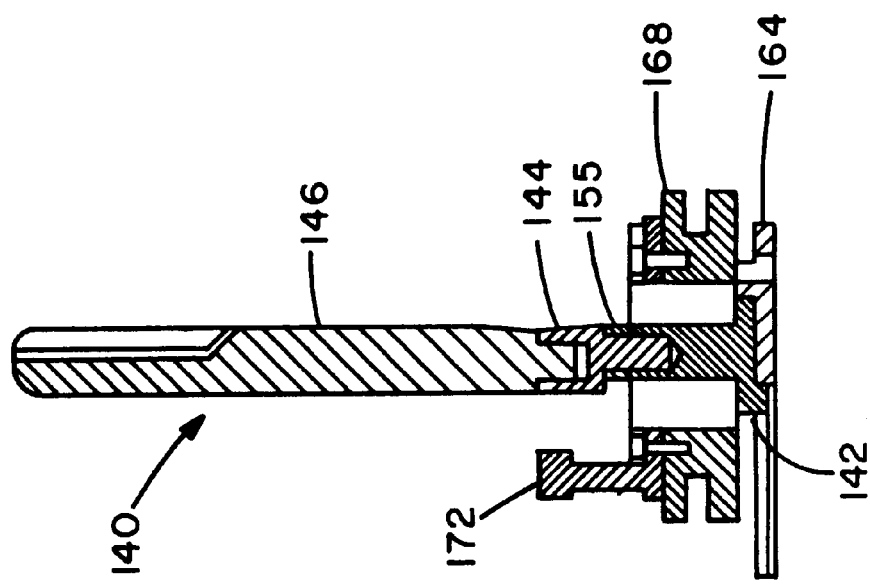
FIG. 22 is a sectional view of the component and tool of FIG. 21.

With the tool 166 assembled about the tibial component 140 as shown in FIG. 22, the angle indicator/wrench key 172 is turned until it indicates the angle previously noted at the step described with reference to FIG. 15. When the angle has been so "dialed in", the offset portion 144 is tightened to the baseplate 142 using the wrench 174 (FIG. 21) on the tightening nut 155. The tibial component is now assembled and ready for implantation. Optionally, if wedge cuts had been made, one or more wedges may be added to the bottom of the baseplate 142 either before or after the assembly of the baseplate, stem, and offset portion.

There have been described and illustrated herein methods and tools for IM revision surgery involving tibial components. While particular embodiments of the invention have been described, it is not intended that the invention be limited thereto, as it is intended that the invention be as broad in scope as the art will allow and that the specification be read likewise. It will therefore be appreciated by those skilled in the art that yet other modifications could be made to the provided invention without deviating from its spirit and scope as so claimed.

What is claimed is:

1. A system for determining the relative location of the IM canal relative to the perimeter of the tibial plateau with the aid of a trial stem inserted in the IM canal and for preparing a tibial component having a baseplate and an offset stem, said system comprising:
   (a) a template approximating the size and shape of a tibial plateau;
   (b) angular indication means coupled to said template for indicating an angle about the center of said template;
   (c) offset bushing means rotatably coupled to said angular indication means, said offset bushing means having positional indicia and a throughbore dimensioned to fit over the trial stem, said throughbore being offset from the center of said bushing means;
   (d) a tibial component adjustment tool having
      (d1) a base portion adapted to be coupled to the baseplate of the tibial component; and
      (d2) a turntable portion adapted to be coupled to the stem of the tibial component, said turntable having angular indication means for indicating the angular offset position of the stem relative to the baseplate wherein rotation of said bushing relative to said angular indication means causes movement of said template relative to said tibial plateau and said positional indicia with said angular indication means indicate the approximate angular position of the center of said template relative to the IM canal and said turntable portion of said adjustment tool is rotatable so said angular indication means indicate the same angle indicated by said positional indicia with said angular indication means.

2. A system according to claim 1 wherein said template comprises a plurality of different sized templates.

3. A system according to claim 2 wherein said angular indication means is adapted to be removably coupled to each of said plurality of different sized templates.

4. A system according to claim 3 wherein said offset bushing means includes a plurality of offset bushing means, each offset bushing means having a throughbore which is offset by a different amount from the center of the offset bushing means, and each offset bushing means is adapted to be removably rotationally coupled to said angular indication means.

5. A system according to claim 1 wherein said template includes means for fixing said template to the tibia.

6. A system according to claim 5 further comprising neutral bushing means adapted to be removably coupled to said template, said neutral bushing means having a throughbore located at the center of said template.

7. A system according to claim 6 wherein said offset bushing means is adapted to be removably rotationally coupled to said angular indication means; and said neutral bushing means is adapted to be removably rotationally coupled to said angular indication means.

8. A system according to claim 1 further comprising a fin punch guide coupled to said template and adapted to receive a fin punch.

9. A system according to claim 8 wherein said angular indication means is adapted to be removably coupled to said template; and said fin punch guide is adapted to be removably coupled to said template.

10. A kit for positioning a tibial base plate having an adjustable offset stem on a resected tibial plateau relative to the location of the medullary canal comprising:

at least two stems for insertion into the canal;

at least two templates approximately the size and shape of a resected tibial plateau, said templates having internal bores having a diameter greater than a diameter of said at least two stems, said bore including angle indicators located around the circumference thereof;

at least two bushings having external diameters matching the inner diameter of said internal bore and each having an internal bores matching the diameter of said stems, a center of said internal bore of said bushings being offset from a center of said internal bore of said templates, whereby rotation of said bushing relative to the center of said internal bore thereof causes movement of said template relative to said plateau; and a tool for adjusting the offset of the stem on said tibial baseplate, said tool having a base portion adapted to be coupled to the baseplate of the tibial component and a rotatable portion coupled to the adjustable offset stem of the tibial component, said rotatable portion having angle indicators corresponding to the angle indicators on said template so that the offset stem can be adjusted to the same offset position as determined by said bushing and template.

11. The kit according to claim 10 wherein said at least two templates comprise a plurality of different size templates.

12. The kit according to claim 11 wherein said angle indicators are located on a separate element adapted to be removably coupled to each of said plurality of different sized templates.

13. The kit according to claim 12 wherein said at least two bushings include a plurality of offset bushings, each offset bushing have a throughbore having a center which is offset by a different amount from a center of said internal bores of said templates and each offset bushing is adapted to be removably rotationally coupled to said internal bore in said templates.

14. The kit according to claim 13 further comprising a neutral bushing adapted to be removably coupled to said template, said neutral bushing having a throughbore located at the center of said bore in said template.

15. The kit according to claim 14 wherein said offset bushing is adapted to be removably rotationally coupled to said angle indicators, and said neutral bushing is adapted to be removably rotationally coupled to said angular indicator means.

16. The kit according to claim 10 wherein said templates include pins for fixing said templates to the tibia.

17. The kit according to claim 10 further comprising a fin punch guide coupled to said templates and adapted to receive a fin punch.

18. The kit according to claim 17 wherein said angular indicator is adapted to be removably coupled to said templates, and said fin punch guide is adapted to be removably coupled to said templates.

19. An instrument for positioning a prosthetic tibial component having a baseplate with an adjustable offset stem extending distally therefrom, relative to the location of the medullary canal in the tibia, said instrument comprising:

a trial stem for insertion into the canal;

a tibial template approximately the size and shape of a resected tibial plateau, said template having an internal opening extending therethrough larger than the diameter of the trial stems, said internal opening having angle indicators around the perimeter thereof;

a bushing having a bore for rotatably receiving said trial stems and an outer circumferential surface having a marker thereon received within said internal opening of said template, said bore in said bushing being offset from a center of said internal opening of said template, whereby rotation of said bushing about said stem causes movement of said template relative to said tibial plateau; and a tool for adjusting the offset of the stem on the tibial baseplate, said tool having a base portion adapted to be coupled to the baseplate of the tibial component and a rotatable portion coupled to the adjustable offset stem of the tibial component, said rotatable portion having angle indicators corresponding to the angle indicators on said template so that the offset stem can be adjusted to the same offset position as determined by said marker and angle indicators on said bushing and template.

20. The instrument according to claim 19 wherein said template comprises a plurality of different size templates.

21. The instrument according to claim 19 wherein said angle indicators are located on a separate element to be removably coupled to each of said plurality of different sized templates.

22. The instrument according to claim 19 wherein a plurality of offset bushings are included, each offset bushing having a throughbore with a center which is offset by a different amount from a center of the internal opening in said template and each offset bushing is adapted to be removably rotationally coupled to said internal bore in said template.

23. The instrument according to claim 22 wherein said template includes pins for fixing said template to the tibia.

24. The instrument according to claim 22 further comprising a neutral bushing adapted to be removably coupled to said template, said neutral bushing having a throughbore located at a center of said internal opening of said template.

25. The instrument according to claim 24 wherein said offset bushing is adapted to be removably rotationally coupled to said angular indicator; and said neutral bushing is adapted to be removably rotationally coupled to said angular indicator.

26. The instrument according to claim 25 further comprising a fin punch guide coupled to said template and adapted to receive a fin punch.

27. The instrument according to claim 26 wherein said angular indicator is adapted to be removably coupled to said template and said fin punch guide is adapted to be removably coupled to said template.

* * * * *

UNITED STATES PATENT AND TRADEMARK OFFICE
CERTIFICATE OF CORRECTION

PATENT NO.    : 6,228,091 B1
DATED         : May 8, 2001
INVENTOR(S)   : Alan Lombardo, Stuart L. Axelson, James V. Bono, and Kenneth A. Krackow It is certified that error appears in the above-identified patent and that said Letters Patent is hereby corrected as shown below:

Title page, Attorney, Agent, or Firm section,
Line 2, "Krumholtz" should read -- Krumholz --.

Column 6,
Line 30, "he" should read -- the --.

Column 9,
Lines 11, 14, and 39, "bore" should read -- bores.
Line 12, "bores" should read -- bore.

Signed and Sealed this

Thirteenth Day of November, 2001

*Attest:*

NICHOLAS P. GODICI
*Attesting Officer*    *Acting Director of the United States Patent and Trademark Office*